United States Patent [19]

Tuthill

[11] Patent Number: 5,063,789
[45] Date of Patent: Nov. 12, 1991

[54] HIGH VELOCITY GAS PARTICULATE SAMPLING SYSTEM

[76] Inventor: Wallace C. Tuthill, 422 Tallowood, Seabrook, Tex. 77586

[21] Appl. No.: 625,344

[22] Filed: Dec. 11, 1990

[51] Int. Cl.$^5$ ............................................. G01N 1/00
[52] U.S. Cl. .................................................. 73/863.23
[58] Field of Search ............... 73/28.01, 28.04, 863.23, 73/863.24, 863.71, 863.81, 863.83, 863.86, 864.52; 55/270

[56] References Cited

U.S. PATENT DOCUMENTS

| | | | |
|---|---|---|---|
| 2,484,202 | 10/1949 | Wintermute | 73/28 |
| 3,083,577 | 4/1963 | Nelson . | |
| 3,408,869 | 11/1968 | Auger . | |
| 3,429,186 | 2/1969 | Price et al. . | |
| 3,487,695 | 1/1970 | Haunschild et al. | 73/863.81 |
| 3,605,485 | 9/1971 | Badzioch et al. | 73/28 |
| 3,653,265 | 4/1972 | Vallino et al. | 73/863.83 |
| 3,774,442 | 11/1973 | Gustavsson | 73/28 |
| 3,784,902 | 1/1974 | Huber | 73/863.23 |
| 4,166,379 | 9/1979 | Bradshaw | 73/23 |
| 4,300,404 | 11/1981 | Mehl et al. | 73/864.52 |
| 4,475,379 | 10/1984 | Jinotti | 73/28 |
| 4,607,228 | 8/1986 | Reif | 324/454 |

Primary Examiner—Robert Raevis
Attorney, Agent, or Firm—Russell E. Schlorff; Harold W. Adams; Edward K. Fein

[57] ABSTRACT

A gas sampling system for determining particulate matter contamination in a high velocity gas flow where the sampling chamber is first cleaned, then evacuated and is coupled by a closed three way valve in a straight line relationship to the gas supply line. The operating gas flow rate is established through the three way valve which is quickly opened to couple the dynamically flowing gas to the evacuated sample chamber in a straight line relationship to trap a gas sample under dynamic conditions. When the sampling chamber has a gas sample the three way valve is again closed so that particulate matter in the sample chamber can be flushed from the sample chamber with a compatible liquid to a filter for collection and analysis.

11 Claims, 1 Drawing Sheet

HIGH VELOCITY GAS PARTICULATE SAMPLING SYSTEM

ORIGIN OF THE INVENTION

The invention described herein was made by an employee of the United States Government and may be manufactured and used by or for the government of the United States of America for governmental purposes without the payment of any royalties thereof or therefor.

FIELD OF THE INVENTION

This invention relates to gas sampling systems and more particularly to sampling systems for capturing and measuring the particulate contamination in a sample of gas obtained from a high velocity gas flow.

BACKGROUND OF THE INVENTION

Gas flow systems which require a high degree of pure gas must be sampled periodically to determine the degree of contamination of the gas. In connection with sampling gas flows for particulate contamination it is common to utilize a fine mesh filter at the exhaust end of a supply system as a trap or catcher for particulate matter that is contained in the gas flowing through the system. The filter, after a period of time, is removed and inspected visually for particulate matter after a known volume of gas flows through the system and the filter. The filter used to catch the particulate matter in the gas flow is typically quite delicate and highly restrictive to the flow of gas in comparison with the supply system. As a consequence, the gas flow rate allowed by the differential pressure across the filter is usually much lower than the operating gas flow rate for the gas supply system. Thus, the sample of particulate matter is taken while the gas flow is at a lower velocity than the operating velocity of the gas flow. A low velocity gas sample is not always representative of the actual cleanliness or contamination of the gas flow in a supply system because the upstream laminar flow in the supply system does not carry all of the particulate matter downstream to the capture filter. As a consequence, some very dirty gas systems can be sampled so delicately that the sample of particulate matter obtained by an exhaust filter inaccurately shows less contamination than the actual contamination of the gas in the system. Thus, trapping of a particulate matter in a filter in an exhaust outlet for determination of contamination is not particularly reliable.

IDENTIFICATION OF THE PRIOR ART

U.S. Pat. No. 2,484,202 issued to H. A. Wintermute on Oct. 11, 1949 (class 73/28) discloses a system where a gas flow in a pipe 28 is periodically interrupted by a damper 34 which periodically diverts a volume of gas for a period of time into an electrostatic precipitation chamber before the damper is closed. While in the precipitation chamber the gas sample is subjected to a high tension current to precipitate out suspended matter from the sample of gas while the sample is trapped.

U.S. Pat. No. 3,083,577 issued to N. A. Nelson, et al. on Apr. 2, 1963 (class 73/422) relates to a fluid sampling system where the flow conduit is divided into two flow passageways. To obtain a sample, spaced apart valves 13 and 14 in one of the passages trap or isolate a sample of fluid in a chamber 17 between the valves. When the sample is isolated by the valves, a discharge valve 15 is opened and a gas drive is used to purge the fluid from the sample chamber. The patent emphasizes that the idea is to trap the sample at turbulent line velocities.

U.S. Pat. No. 3,408,869 issued to F. B. Auger on Nov. 5, 1968 (class 73/421.5) relates to a system for monitoring the vapor within the outlet pipe of a chemical reactor. The sampler is connected as a bypass to a stream of a reactor output vapor. A carrier gas which is inert to the components and to the reactor output vapor under the prevailing conditions is passed continuously into the apparatus through three ports at a very low flow rate so that no diffusion of reactor vapor occurs through the three ports. When a sample is required, high pressure gas is admitted to the two outermost ports to divert a volumetric sample of the gas from a center port to a gas chromatograph.

U.S. Pat. No. 3,429,186 issued to J. L. Price, et al. on Feb. 25, 1969 (class 73/421.5) relates to a gas sampling system where a timer opens bypass valves and a side stream of gas flows through a conduit and the pressure of the sample is balanced to the line pressure.

U.S. Pat. No. 3,605,485 issued to S. Badzioch, et al. on Sept. 20, 1971 (class 73/28) relates to a device for passing a stream of gas containing dust into a centrifugal flow separating device for monitoring the dust concentration in a gas sample.

U.S. Pat. No. 3,774,442 issued to Gustavsson on Nov. 27, 1973 (class 73/28) relates to a device for sampling particle concentration in a flow of gas where the sampling device is inserted into a gas flow line for taking the sample. The front end portion of the sampler includes a through flow body so that part of the gas flow is passed through a diffuser channel to a screen filter arranged at the downstream end of the through flow body and the gas flow is arranged to return to the gas duct. The device is similar to a vacuum sweeper bag which is intended for gross magnitude particulate checks without chemical analysis of the gas.

U.S. Pat. No. 4,166,379 issued to R. F. D. Bradshaw on Sept. 4, 1979 (class 73/23) relates to an apparatus for detecting the presence of volatile or organic substances which uses electrical currents passed through a filament.

U.S. Pat. No. 4,475,379 issued to Jinotti on Oct. 9, 1984 (class 73/28) is a pollen encounter where pollen grains are deposited on the edge of a glass slide as the air flows through the tube.

U.S. Pat. No. 4,607,228 issued to R. B. Reiff on Aug. 19, 1986 (class 324/454) relates to an apparatus for measuring the concentration of solid particles in a fluid stream by utilizing electrical charging of the particles of gas and a charge measuring device.

SUMMARY OF THE INVENTION

The present invention is embodied in a gas sampling system which is adapted for coupling to a gas supply line where a gas flow at the operating gas flow rate can be established through a three way valve to discharge at a right angle to the normal direction of gas flow. The three way valve is part of a gas sampling chamber which includes a tubing coil and an exit valve which is coupled to a particulate matter filter. With the three way valve in a position closing off the sampling chamber, a purging system 34 can be connected through valves to flush and clean the sampling chamber. After cleaning the sampling chamber, a vacuum system draws a vacuum on the sampling chamber. With the operating gas flow rate established, the three way valve is quickly operated to provide a straight line flow of gas through the three way valve into the evacuated sampling chamber. When the pressure in the sample chamber equalizes to the line pressure, the three way valve is closed and the exit valve opened to release the gas sample through the filter. A clean solvent is then pumped through the sampling chamber to remove and to deposit particulate matter from the gas sample in the filter. With a known volume of gas sample, the degree of contamination can be determined from the count of the particulate matter.

DESCRIPTION OF THE DRAWINGS

The drawing illustrates a gas sampling system for determining the contamination factor in a dynamic gas flow system.

DESCRIPTION OF THE PRESENT INVENTION

Figure 1:
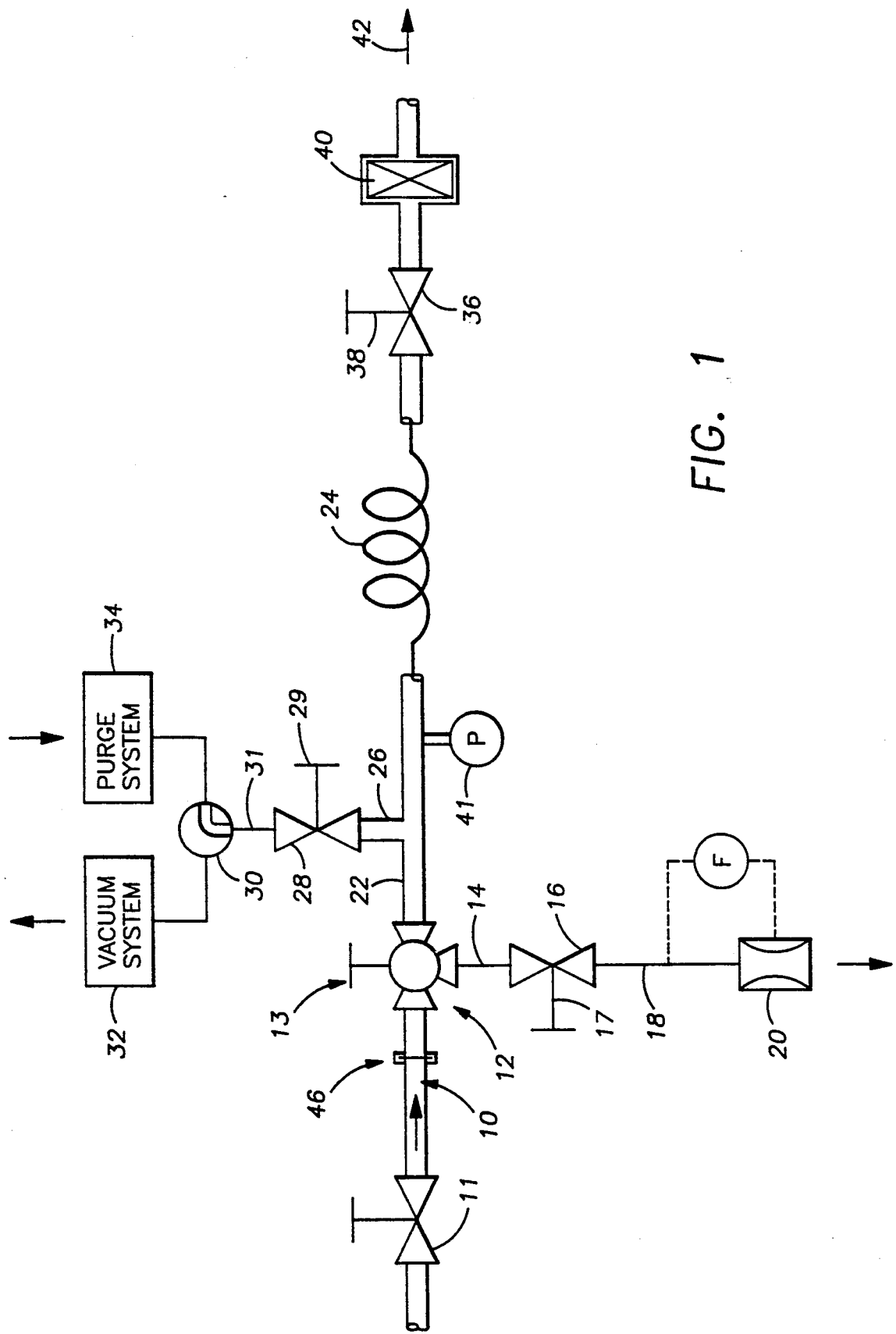

In the present system for sampling a gas flow for contamination, the flow of gas is sampled at an exhaust pipe 10 of a gas supply flow line. While sampling at an exhaust outlet is the form of the invention shown, the principles of the present invention are also applicable to in line sampling using a parallel sampling line to the main line.

The exhaust pipe 10 couples shutoff valve 11 to a three way ball valve 12 which diverts gas flow (in one position) to a right angle port of the ball valve 12. Valve 12 is operated by positioner 13 by manual or remote control means. The right angle port of the ball valve 12 is coupled by conduit 14 to a throttle or gas rate valve 16. The throttle valve 16 is operable either by manual or remote control means 17 to open and close off the conduit 14. The throttle valve 16 is connected by a conduit 18 to a flow meter venturi 20 which exhausts to atmosphere. The flow meter gauge F will provide an indication of gas flow rate or gas velocity.

The in line port of the three way ball valve 12 is attached by a conduit 22 to a spirally wound tubing coil 24. The tubing coil 24 is spirally wound for compactness and defines a sample chamber. A "T" connection 26 is closely coupled to a control valve 28 which has either a manual or remote control means 29 to open and close off the conduit 22. The control valve 28 couples to a switch valve 30 which selectively connects an input conduit 31 either to a vacuum pump system 32 or to a liquid pump or purge system 34.

The output of the tubing coil 24 is connected by an exit valve 36 to a particle filter 40 sized to capture fine particles entrained in a gas flow. The exit valve 36 has either a manual or remote control means 38 to open and close the tubing coil 24 relative to the filter 40.

In the foregoing system, the diametric size of the tubing coil 24 should be great enough to obtain a representative capture cross sectional area. The purge system 34 should be large enough to allow effective flushing and cleaning prior to and after a gas capture sequence. The length of the tubing coil 24 should be enough to capture a significant volume, and the exact tubing/valving sample volume in the tubing coil 24 and tee 26 should be predetermined to be able to relate the captured particulate matter in the filter 40 to a known volume of gas captured in the tubing coil 24.

The sampling operation is carried out in the following manner. The three way valve 12 is initially in a position coupling the pipe 10 to the right angle conduit 14 and the gas rate valve 16 is initially closed.

The control valve 28 is opened while the switch valve 30 is in the position shown. When the exit valve 36 is opened, a flush fluid such as isopropyl alcohol or other compatible, volatile solvent is passed through the tee 26, the capture tubing coil 24, the exit valve 36 and the particle filter 40 to exhaust as shown at 42 to a container (not shown). The fluid from the exhaust 42 can be coupled to a recirculatory pump and system (not shown) to reintroduce the flush fluid to the purge system 34 if desired. After pumping flush fluid through the filter 40, the system is shut down and the filter 40 is examined to determine if the tubing coil 24 is clean. The flushing process is continued until the tubing coil 24 is clean.

After the tubing coil 24 is clean, the flush fluid is purged from the tubing with gas and the exit valve 36 is closed. The switch valve 30 is shifted to a position where the vacuum system 32 can evacuate the tubing coil 24 through the control valve 28 to less than 0.1 mm Hg. When the tubing coil 24 is evacuated and all fluid dried from the tubing 24, the control valve 28 is closed. This leaves the tubing coil 24 as a clean, dry, evacuated sample chamber.

To commence gas flow through valve 12, the gas rate valve 16 is opened so that there is a right angle diversion of gas flow from the pipe 10, through valve 12, manifold 14, the gas rate valve 16, and the flowmeter venturi 20. The flow rate is adjusted to the operating gas flow rate and the valve 12 is quickly shifted to its other position where the gas flow path from the pipe 10 is straightened and high velocity particles in the on going gas flow are carried into the tubing coil 24 by both gas entrainment and momentum. When the pressure becomes equalized in the tubing coil 24, as indicated by a pressure gauge 41, the ball valve 12 is returned to its original position and the gas rate valve 16 is closed.

The exit valve 36 is then opened slowly (to avoid damage to filter 40) which relieves the gas pressure in the tubing coil 24 and the control valve 28 and the switch valve 30 are operated to provide a liquid to flush the tubing coil 24 with a clean solvent liquid with the solvent liquid passing through the filter 40. After flushing the particulate matter in the tubing coil 24 to the filter 40, the total amount of the particulate matter collected in the filter 40 can be related to or determined to be related to the volume of gas in the sample chamber (tubing coil 24 plus tee 26) as an indication of contamination in the gas flow.

The foregoing system can be arranged for portability with a quick connect/disconnect 46 for releasable coupling to a pipe 10. The shutoff valve 11 can be utilized whenever the system is attached and detached from the pipe 10.

It will be apparent to those skilled in the art that various changes may be made in the invention without departing from the spirit and scope thereof and therefore the invention is not limited by that which is enclosed in the drawings and specifications, but only as indicated in the appended claims.

I claim:

1. A high velocity gas sampling apparatus including:
   gas sample chamber receiving a dynamic gas flow while in an evacuated condition;
   first means for selectively coupling a dynamic gas flow in an in-line flow relationship to one end of said gas sample chamber by use of a valve;

second means at the other end of said gas sample chamber for selective discharge of said gas sample chamber by use of a valve;

means for filtering coupled to said second means for receiving a discharge output from said gas sample chamber when said second means are discharged;

means for evacuating said gas sample chamber prior to opening said first means; and means for removing residual contaminate material from said gas sample chamber after said second means are discharging and passing said contaminate material to said filtering means.

2. The apparatus as set forth in claim 1 wherein said sample chamber includes a tubular pipe member with a cross sectional area and length sized to obtain a representative volume of a dynamic gas sample.

3. The apparatus as set forth in claim 2 wherein said pipe member is a spirally arranged tubing.

4. The apparatus as set forth in claim 1 wherein said first valve means is a three way valve with two ports arranged in-line to communicate a dynamic gas flow in a straight line condition to said gas sample chamber means in one position of said first valve means.

5. The apparatus as set forth in claim 1 wherein said first means has three ports with a first one of said ports being disposed at a right angle to said other two ports which are in line with one another, a flow rate device coupled to said first port, said first means having another position for directing gas flow through said flow rate device for obtaining a dynamic gas flow at a selected flow rate.

6. The apparatus as set forth in claim 5 wherein said flow rate means includes a throttle valve and a flowmeter.

7. The apparatus as set forth in claim 1 including a third means for selectively coupling said evacuating means and said flushing means to said gas chamber by use of a valve.

8. A method of obtaining a gas sample from a high velocity gas stream comprising the steps of:

locating a sample chamber for collecting a discrete gas sample of a known volume in an in-line relationship to the high velocity gas stream to be sampled where said sample chamber has sufficient volume to obtain a representative gas sample;

evacuating said sample chamber;

passing the high velocity gas stream into said sample chamber and trapping a discrete gas sample in said sample chamber;

releasing the discrete gas sample in said sample chamber through a filtering means constructed and arranged to collect contaminate particle matter;

flushing the sample chamber with a liquid and flowing the liquid from the sample chamber through the filtering means sized to collect contaminate particle matter; and determining the amount of contaminate particle matter in the filtering means relative to the volume of said sample chamber.

9. The method as set forth in claim 8 wherein said sample chamber is coupled to a three way valve where said three way valve in one position provides bypass flow and said three way valve in another position provides for in-line high velocity gas flow into said sample chamber.

10. The method as set forth in claim 9 wherein said sample chamber is coupled to other means where said other means in one operating position evacuates said sample chamber and in another operating position connects the flushing liquid to said sample chamber.

11. A method of obtaining a gas sample from a high velocity gas stream comprising the steps of:

coupling a spirally arranged tubing member by a three way valve to a source of high velocity gas flow where the three way valve in one operating position permits dynamic gas flow and in a second operating position couples high velocity gas flow in an in-line relationship to said tubing member in said evacuated condition for receiving a high velocity gas flow sample;

flushing the spirally arranged tubing member with a liquid to clean the interior of the tubing to received a high velocity gas sample;

evacuating the tubing member to an evacuated condition prior to receiving a high velocity gas sample;

operating said three way valve for obtaining a discrete volume of high velocity gas flow sample in said tubing member;

exhausting said gas flow sample from said tubing member through a particulate matter filter;

flushing said tubing member with a liquid to move any particulate matter remaining in said tubing member to the particulate matter filter; and determining the amount of particulate matter in the particulate matter filter relative to the discrete volume of high velocity flow sample.

* * * * *